(12) United States Patent
Bamberg et al.

(10) Patent No.: US 10,076,879 B2
(45) Date of Patent: Sep. 18, 2018

(54) METHOD AND DEVICE FOR THE GENERATIVE PRODUCTION OF A COMPONENT

(75) Inventors: Joachim Bamberg, Dachau (DE); Wilhelm Satzger, Munich (DE); Thomas Hess, Munich (DE)

(73) Assignee: MTU AERO ENGINES AG, Munich (DE)

( * ) Notice: Subject to any disclaimer, the term of this patent is extended or adjusted under 35 U.S.C. 154(b) by 540 days.

(21) Appl. No.: 14/237,206

(22) PCT Filed: Jul. 31, 2012

(86) PCT No.: PCT/DE2012/000768
§ 371 (c)(1),
(2), (4) Date: Feb. 5, 2014

(87) PCT Pub. No.: WO2013/025581
PCT Pub. Date: Mar. 7, 2013

(65) Prior Publication Data
US 2014/0159266 A1 Jun. 12, 2014

(30) Foreign Application Priority Data
Aug. 27, 2011 (DE) .......................... 10 2011 111 818

(51) Int. Cl.
*B29C 64/386* (2017.01)
*B29C 67/00* (2017.01)
(Continued)

(52) U.S. Cl.
CPC ........ *B29C 67/0085* (2013.01); *B22F 3/1055* (2013.01); *B23K 26/34* (2013.01);
(Continued)

(58) Field of Classification Search
CPC ............ B29C 67/0085; B29C 67/0088; B29C 67/0077; B29C 64/386; B29C 64/20;
(Continued)

(56) References Cited

U.S. PATENT DOCUMENTS

| | | | |
|---|---|---|---|
| 2004/0139805 A1 | 7/2004 | Antonelli et al. | |
| 2007/0176312 A1* | 8/2007 | Clark | B22F 3/1055 264/40.1 |

(Continued)

FOREIGN PATENT DOCUMENTS

| | | | |
|---|---|---|---|
| DE | 3723609 A1 | 1/1988 | |
| DE | 19835860 C1 | 4/2000 | |

(Continued)

OTHER PUBLICATIONS

NPL-1. Deep Penetrating Eddy Currents and Probes. 2006. ECNDT.*
(Continued)

*Primary Examiner* — Yogendra N Gupta
*Assistant Examiner* — Leith S Shafi
(74) *Attorney, Agent, or Firm* — Barlow, Josephs & Holmes, Ltd.

(57) ABSTRACT

A method for the generative production of a component and a device for carrying out such a method, includes the following steps: applying a material layer with a constant layer thickness; solidifying a region of the material layer according to a component cross section; generating an eddy-current scan of the solidified region, a scan depth corresponding to a multiple of the layer thickness; determining a material characterization of the solidified region taking into consideration a previous eddy-current scan of solidified regions of lower-lying material layers; and repeating the steps until the component is assembled. An electric material characterization of each individual layer is determined using a recursive algorithm of individual measure- (Continued)

ments (monolayer by monolayer), and thus the entire component is tested step by step completely in a highly resolved manner.

12 Claims, 2 Drawing Sheets

(51) Int. Cl.
| | |
|---|---|
| B29C 64/20 | (2017.01) |
| B29C 64/153 | (2017.01) |
| B22F 3/105 | (2006.01) |
| B23K 31/12 | (2006.01) |
| G01N 27/90 | (2006.01) |
| B23K 26/34 | (2014.01) |
| B23K 26/70 | (2014.01) |

(52) U.S. Cl.
CPC .......... *B23K 26/702* (2015.10); *B23K 31/125* (2013.01); *B29C 64/153* (2017.08); *B29C 64/20* (2017.08); *B29C 64/386* (2017.08); *B29C 67/0077* (2013.01); *B29C 67/0088* (2013.01); *G01N 27/902* (2013.01); *G01N 27/904* (2013.01); *B22F 2003/1057* (2013.01); *Y02P 10/295* (2015.11)

(58) Field of Classification Search
CPC .... B29C 64/153; B23K 26/702; B23K 26/34; B23K 31/125; G01N 27/904; G01N 27/902; B22F 3/1055; B22F 2003/1057; Y02P 10/295

USPC ..... 264/40.1, 40.4, 406, 405, 407, 408, 409, 264/410, 411; 425/169, 171, 174, 174.2, 425/174.4, 174.8 R, 174.8 E, 173; 73/60, 73/762, 763, 774, 778, 779, 862.626, 73/861.08, 861.11, 861.17; 15/94; 700/90, 108–109, 117–119
See application file for complete search history.

(56) References Cited

U.S. PATENT DOCUMENTS

| | | | | |
|---|---|---|---|---|
| 2011/0006761 | A1* | 1/2011 | Redko | .................. G01N 27/904 324/239 |
| 2011/0120494 | A1* | 5/2011 | Ifuku | .................... B06B 1/0648 134/1 |

FOREIGN PATENT DOCUMENTS

| | | |
|---|---|---|
| EP | 1815936 A1 | 8/2007 |
| EP | 1815936 B1 | 11/2009 |
| JP | 2005262218 A | 9/2005 |

OTHER PUBLICATIONS

Antonelli, G. et al., "Qualification of a frequency scanning eddy current equipment for nondestructive characterization of new and serviced high-temperature coatings," International Gas Turbine & Aeroengine Congress & Exhibition, New Orleans, LA—Jun. 4-7, 2001, XP009007444.

* cited by examiner

METHOD AND DEVICE FOR THE GENERATIVE PRODUCTION OF A COMPONENT

BACKGROUND OF THE INVENTION

The invention relates to a method for the generative production of a component and a device for carrying out such a method.

In a generative production process such as SLM (Selective Laser Melting), defects in the component may arise due to different causes. The defects may lead to a reduction in the quality of the component and are conventionally found only by testing the finished component. Examples of defects are microcracks, foreign inclusions, and undigested material. The tests are either destructive or non-destructive. Destructive tests, however, require the production of a large number of components or test specimens. Non-destructive test methods such as, e.g., x-ray computed tomography, are technically complex, time-consuming and costly. Actually, by monitoring the temperature and the geometry of the melting bath, conclusions relative to the component can be drawn indirectly, but this testing technique does not make possible a more precise control of the material properties and the recognition of defects.

A method for non-destructive process control during generative production is described in the publication EP 1 815 936 B1. In this method, an ultrasound testing is conducted during the production. Optionally, an eddy-current testing may accompany the ultrasound testing. A disadvantage in this method, however, is that a plurality of material layers are detected or scanned by the sound field and/or the eddy field and thus individual material layers cannot be accurately detected. Ultrasound testing also requires a complex system control. Actually, eddy-current testing can basically be operated with a penetration depth such that individual material layers can be detected exclusively. But test frequencies are necessary to do this that require, for example, a calibration of the eddy-current sensors that cannot be justified with reasonable expenditure, as well as lift-off effects.

BRIEF SUMMARY OF THE INVENTION

The object of the invention is to create a method for the generative production of a component that eliminates the above-named disadvantages and permits a material characterizing of individual material layers as well as a device for carrying out such a method.

This object is achieved by a method and device according to the present invention.

In a method according to the invention for the generative production of a component, a material layer having a constant layer thickness is applied first. Then a region of the material layer is solidified according to a component cross section. After this, an eddy-current scan of the solidified region is generated, whereby a scanning depth corresponds to a multiple of the layer thickness. Then a material characterization of the solidified region is determined, taking into consideration a preceding eddy-current scan of solidified regions of lower-lying material layers. Then, the preceding steps are repeated until the component is completely assembled.

It is possible with the method according to the invention to characterize a component completely through its entire volume, material layer by material layer. After finishing the component, a complete, high-resolution, 3-dimensional "x-ray exam" and material characterization by means of eddy current is present. The expenditure for quality assurance is reduced, since complicated and less precise post-investigations of the finished component are dispensed with. The material layers usually have a layer thickness of 20 μm to 40 μm and are thus essentially smaller than one penetration depth of the eddy field. The material characteristics of each individual material layer are determined in a non-destructive manner by means of signal analysis, in particular a differentiation of the 3D eddy-current scanning data of the material layers on top of one another. The 3D eddy-current scanning data can be differentiated in space in a freely selectable manner. For example, the differentiation can be carried out in the direction of a mechanical principal load for evaluating material discontinuities. The eddy-current scanning data provide insights, for example, on the measured electrical conductivity and permeability as well as information on the porosity, type of defects, extent of melting, and texture, among other things.

Since the penetration depth of the eddy field decreases exponentially with depth, in order to achieve a particularly precise measurement result, it is advantageous if a weighting of the material layers is considered in the comparison of the eddy-current scans or the eddy-current scan data.

In order not to prolong the production time of the component by means of the eddy-current testing, each eddy-current scan is produced preferably during the application of a new material layer. In this case, it has been shown that the powder particles that have not melted together in the new material layer as well as the powder bed surrounding the component are not detected by the eddy-current scan.

Preferably, the eddy-current scans are conducted in a frequency range from 1 MHz to 10 MHz. In this way, a scanning depth of approximately 0.5 mm is achieved, by which means approximately 10 to 20 material layers are scanned simultaneously. Such a frequency range is well controllable and does not require, for example, a complicated sensor calibration.

A multi-frequency measurement can be carried out in each eddy-current scan for the highly precise evaluation of the defects.

Eddy-current microscans can be carried out in order to further increase the precision of the test method according to the invention. For this purpose, several images of one material layer can be recorded for each eddy-current scan with an offset of less than one sensor distance.

In addition to a 100% testing and characterizing of the component, the eddy-current scanning data can also be utilized for the monitoring, control, and regulating of the generative manufacturing process. For example, the determined material characterization can be used in real time for the correction of process parameters, so that defects are not only recognized, but their growth is inhibited.

An effective cleaning of the eddy-current sensors can be achieved, for example, by means of a shaking motion. This type of cleaning has the advantage that the use of brushes or the like is superfluous.

A device according to the invention for carrying out a method according to the invention has a mobile eddy-current array for scanning a solidified region of a material layer relative to the component to be manufactured, wherein a scanning depth corresponds to a multiple of the layer thickness, and an evaluating system is used for determining a material characterization of the solidified region, taking into consideration a preceding eddy-current scan of solidified regions of lower-lying material layers. The eddy-current array and the evaluating system can be integrated into the device in a minimally invasive manner.

Preferably, the eddy-current array is positioned on the back side of a doctor blade. The precision of the doctor blade in the form of a highly precise, minimal distance to the already partially constructed component is quasi-transferred to the eddy-current array by means of the arrangement of the eddy-current array on the doctor blade.

Preferably, the eddy-current array is an eddy-current linear array, which extends in the longitudinal direction of the doctor blade. On the one hand, the eddy-current array extends in this manner continually over the entire component to be manufactured. On the other hand, due to the linear form, the sensors are closely positioned on the doctor blade, so that the doctor blade provided with the eddy-current array travels the same distance or nearly the same distance for each layer application as a doctor blade without an eddy-current array.

The eddy-current array can provide a plurality of individual sensors or half-transmission sensors in a hexagonal arrangement, for example. In particular, by means of using half-transmission sensors, a transmitting and receiving electronic system can be designed in a technically simple manner, since each half-transmission sensor or each half-transmission coil can transmit as well as receive. Also, a half-transmission sensor has a single sharply pronounced maximum when compared to the individual sensor.

For cleaning the eddy-current array by means of a shaking motion, the device may have a shaking mechanism with at least one piezoelement that is mechanically connected to the eddy-current array in an operative manner.

In order to continually have an optimal distance from the eddy-current array to the partially constructed component, the device can have an automatic distance control mechanism for adjusting the distance from the eddy-current array to the respective uppermost material layer that is solidified in sections.

Other advantageous embodiment examples of the invention are the subject of additional subclaims.

Preferred embodiment examples of the invention are explained in more detail in the following, based on very simplified schematic illustrations. Here:

DETAILED DESCRIPTION OF THE INVENTION

Figure 1:
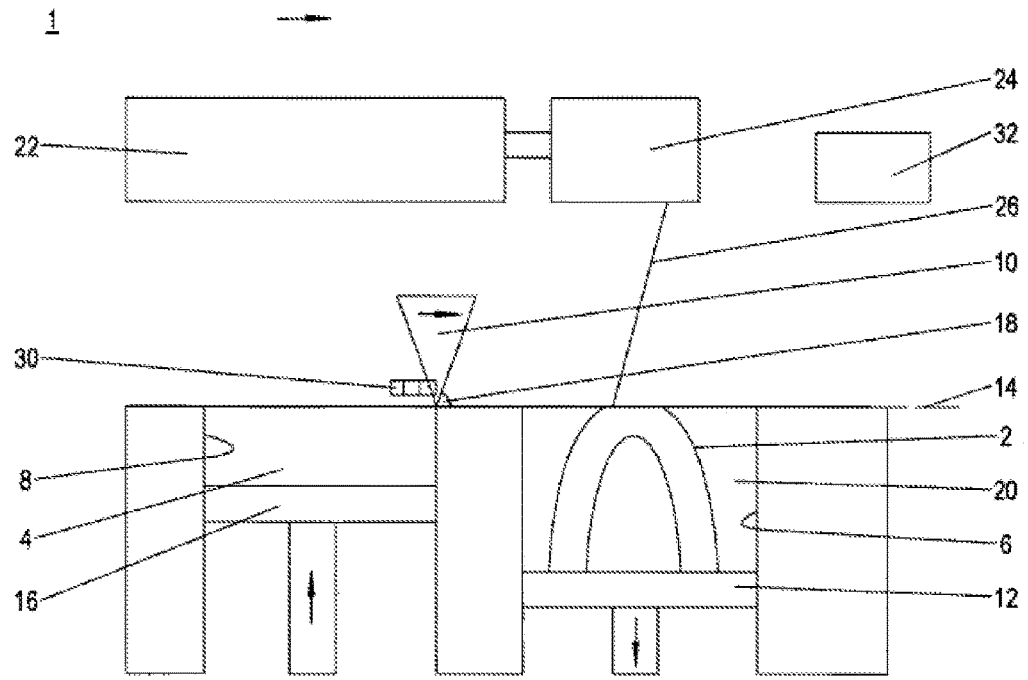
FIG. 1 shows an illustration of a device according to the invention for the production of a component according to the invention.
Figure 2A:
FIGS. 2a to 2e show examples of defects of the component.
Figure 2B:
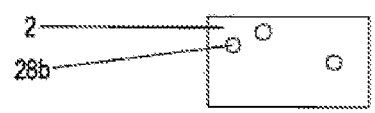
Figure 2C:
Figure 2D:
Figure 2E:

A device 1 according to the invention for the generative production of a component 2 is shown in FIG. 1. The component 2, for example, is a component of an aircraft engine and is constructed layer by layer from a metal powder 4 in the so-called Selective Laser Melting process.

The device 1 has a working chamber 6, a powder space 8, and a doctor blade 10.

The component 2 is built up layer by layer in the working chamber 6. It is bounded on the bottom by a lowering piston 12, which can be lowered in the vertical direction in order to adjust a working plane 14.

The powder space 8 serves for providing the powder 4. It is bounded on the bottom by a lifting piston 16, which can be raised into the working plane 14 in the vertical direction for subsequent guiding of powder 4.

The doctor blade 10 serves for introducing the powder 4 from the powder space 8 into the working chamber 6. It executes a displacement motion in the working plane 14 and oriented from left to right according to the representation in FIG. 1, by means of which motion, it introduces the powder 4 or a quantity of powder 18 for one powder or material layer of the component 2 from the powder space 8 into the working chamber 6. Since the powder 4 is introduced over the entire cross section of the working chamber 6 lying in the working plane 14, but only the region of the respective material layer that depicts a cross-sectional surface of the component 2 is solidified, a powder bed 20 is formed around the component 2.

In order to solidify the respective region of the material layers, the device 1 has a laser system 22 and an optics system 24 interacting with the laser system 22, by means of which a laser beam 26, which is produced by the laser system 22, and which corresponds to the respective cross-sectional surface, can be guided over the material layer.

According to the invention, during the production of the component 2, an eddy-current testing is carried out in real time, or an online eddy-current testing of the last solidified region of the material layer is conducted. The testing serves for recognition of defects 28, for example, such as microcracks 28a, micropores 28b, segregations 28c, foreign inclusions 28d, or unmolten material 28e, which are shown in FIGS. 2a to 2e. For conducting the testing, the device 1 has an eddy-current array 30 and an evaluating system 32, which are shown in FIG. 1.

Figure 3:
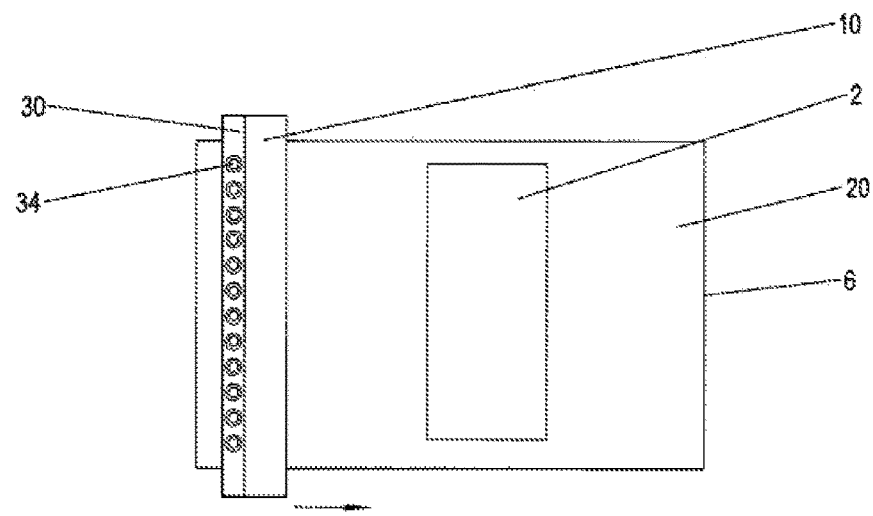
FIG. 3 shows a top view onto a powder bed of the device.

The eddy-current array 30 serves for the generation of an eddy-current scan and is arranged on the back of the doctor blade 10. As is shown in FIG. 3, it is an eddy-current linear array, which extends in the longitudinal direction of the doctor blade 10 and is composed of a plurality of sensors 34 disposed behind one another. The sensors 34 are embedded in a high-temperature plastic and designed as half-transmission sensors or half-transmission coils for reducing the expenditure for transmitting and receiving electronics.

In order to adjust an optimal distance from the eddy-current array 30 to the working plane 14 or to the uppermost solidified material layer, segment by segment, the device 1 provides an automatic distance control mechanism (not shown).

For cleaning the eddy-current array 30, the device 1 has a shaking mechanism (not shown) having at least one piezoelement. The shaking mechanism interacts mechanically with the eddy-current array 30 and displaces the eddy-current array 30 in a shaking motion by means of a control, whereupon the powder 4, which has not been deposited on the sensors 34, falls away.

The evaluating system 32 determines a material characterization of the solidified regions of the material layers from a current eddy-current scan, taking into consideration a preceding eddy-current scan of solidified regions of deeper-lying material layers. For this purpose, the evaluating system 32 uses a recursive algorithm, which, on the one hand, considers the imaging precision recorded with increasing scanning depth or penetration depth of an eddy field. The penetration depth in FIG. 3 runs orthogonal to the plane of the drawing and is provided with the reference symbol z in FIGS. 4 and 5. On the other hand, the recursive algorithm considers that the material layers occupy a greater depth position with each new powder application, or are further removed from the respective uppermost material layer. The evaluating system 32 communicates with a system control of the device 1 and thus makes possible a monitoring of the control and regulation of the generative manufacturing process, in addition to a monitoring of the material layers. For example, the determined material characterization can be used in real time for the correction of process parameters, so that recognized defects 28 can be evaluated with respect to their effects, their growth can be inhibited, and further defects 28 of the same type can be prevented.

Figure 4:
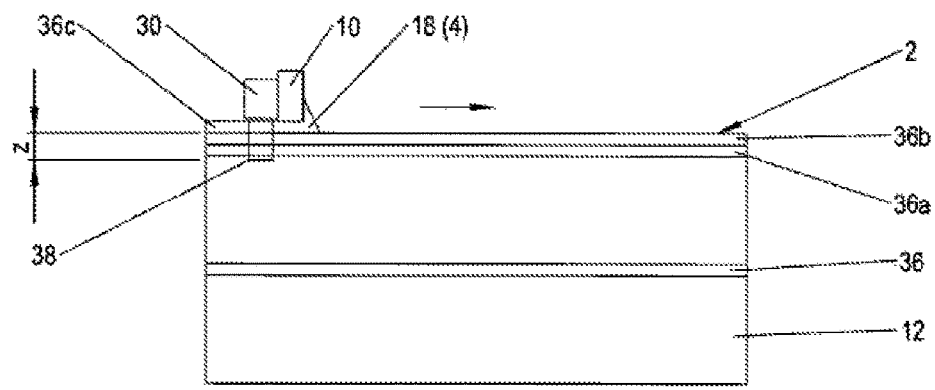
FIG. 4 shows a method step n for carrying out the method according to the invention.
Figure 5:
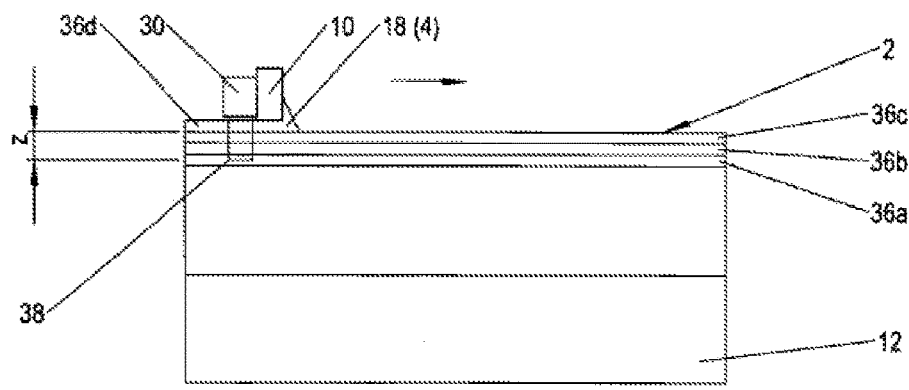
FIG. 5 shows a method step n+1 of the method according to the invention.

In the following, a method according to the invention for the production of the component 2 with a testing of the component 2 during the production will be explained on the basis of FIGS. 4 and 5. The component 2 will be built up from a plurality of material layers, of which two material layers 36a, 36b are numbered for reasons of simplicity in FIG. 4. Each material layer 36a, 36b is composed of a powder 4, which, after being applied, is solidified only in the regions that depict a cross section of the component 2. After the solidification, section by section, of the respective last applied or uppermost material layer 36b, a new material layer 36c is built up from the powder 4. The powder 4 is applied each time by the doctor blade 10 in a constant layer thickness of approximately 20 μm to 40 μm onto the preceding and initially uppermost material layer 36b.

For applying the powder 4 in the method of the doctor blade 10, the eddy-current array 30 is guided with it by being connected to the back of doctor blade 10, and this generates an eddy field 38 having a penetration depth z. Preferably, the eddy-current array 30 is operated in a frequency range of 1 MHz to 10 MHz and thus generates an eddy field 38 with a penetration depth of approximately 0.5 mm, which corresponds to a multiple of the layer thickness. A plurality of material layers 36a, 36b are scanned simultaneously in this way. The eddy field 38, however, decreases exponentially with the penetration depth z, so that the uppermost material layer 36b, which is shown in FIG. 4, forms an intermediate material layer 36b after applying and solidifying by section another material layer 36c, and thus has a smaller weighting in the eddy-current scan of the material layer 36c (FIG. 5) than in its own eddy-current scan (FIG. 4). The result of each eddy-current scan is an averaged electrical material characterization of the component 2 through a penetration depth z, which comprises approximately 10 to 20 material layers 36a, 36b, 36c in the selected frequency range. Unsolidified material layers (FIG. 4, material layer 36c; FIG. 5, material layer 36d) as well as the unsolidified powder bed 20 are not detected by the eddy-current scan and are thus not imaged. After conducting an eddy-current scan, a material characterization of the respective uppermost material layer 36b (FIG. 4) or 36c (FIG. 5) is prepared with the use of the recursive algorithm, wherein the weighting of the material layers 36a, 36b, 36c, which decreases with the penetration depth z, and the varying depth position of the material layers 36a, 36b, 36c, is considered after each new layer application. In other words, with reference to FIG. 5: The recursive algorithm determines a material characterization of the solidified region of the respective uppermost material layer 36c taking into consideration an actual eddy-current scan over the material layers 36a, 36b, 36c and a preceding eddy-current scan of solidified regions of the deeper-lying material layers 36a, 36b. For each new layer application, a preceding material layer is thus tested completely and in a highly resolved manner. These steps are repeated until the component 2 is completely assembled. Of course, with the recursive algorithm, it is also considered that when a first material layer 36 is applied onto lowering piston 12, comparative eddy-current scan data are not yet present, as is illustrated in FIG. 4.

The eddy-current array 30 is moved corresponding to the doctor blade 10, but a so-called eddy-current microscan can be conducted in order to increase the resolution of the eddy-current scan, by which superimposed eddy scan images can be recorded with a displacement of less than the distance between adjacent sensors 34.

A multi-frequency measurement can be carried out with each eddy-current scan for a highly precise evaluation of the defects.

If a defect 28 is encountered, for an accurate evaluation of it and its effect, the data for the 3D eddy-current scan can be merged into a voxel data set, and a comparison with construction data, such as 3D-CAD data of the component 2, can be carried out. Additionally, a differentiation of the 3D eddy-current measurement data can be conducted in freely selectable space for the evaluation of the defects 28. For example, for the evaluation of unmolten material 28e, a differentiation can be produced in the direction of the mechanical principal load.

Also, analyses of the 3D eddy-current scan data relative to material characterizations between adjacent material layers and within the individual material layers are preferably carried out for determining texture and for ascertaining internal stresses of the component 2. Further, an eddy-current comparison is produced with parallelly constructed reference test units.

Further, the powder 4 is preferably evaluated with respect to its powder quality, e.g., relative to foreign inclusions and uniformity of the respective powder application.

Additionally, the material characterization of the component 2 is preferably utilized for monitoring, control, and regulation of the generative production. In particular, the material characterization is used for the correction of process parameters in real time.

A method is disclosed for the generative production of a component, in which an electrical material characterization of each individual layer is determined by means of a recursive algorithm from individual measurements (monolayer by monolayer), and thus the entire component is tested completely and in a highly resolved manner, step by step, as well as a device for carrying out such a method.

The invention claimed is:

1. A method for the generative production of a component, comprising the steps of:
   a) applying a powder material for the formation of a new material layer with a constant layer thickness;
   b) producing an eddy-current scan during step a), wherein a scanning depth corresponds to a multiple of the constant layer thickness;
   c) solidifying a region of the powder material to form the new material layer according to a component cross section;
   d) determining a material characterization of an uppermost material layer of the solidified region by comparing a preceding eddy-current scan of the solidified region with the current eddy-current scan of the solidified region, wherein the preceding eddy-current scans of solidified region is weighted exponentially according to depth, wherein defects comprising microcracks, micropores, segregations, foreign inclusions, and unmolten material are identified in the uppermost material layer of the solidified region;

e) isolating the uppermost material layer of the solidified region from the current eddy-current scan of step b) with a recursive algorithm that is a function of the current eddy-current scan as compared to the preceding eddy-current scan; and f) repeating the steps a) to e) until the component is assembled.

2. The method according to claim 1, wherein the eddy-current scans are carried out in a frequency range of 1MHz to 10MHz.

3. The method according to claim 1, wherein a multi-frequency measurement is conducted for each eddy-current scan.

4. The method according to claim 1, wherein several images of one material layer are recorded and superimposed to form a complete image of the solidified region for each eddy-current scan.

5. The method according to claim 1, wherein the determined material characterization is used in real time for the correction of process parameters.

6. The method according to claim 1, further comprising cleaning a plurality of eddy-current sensors with a shaking motion.

7. A device for the generative production of a component, comprising, an eddy-current array, which can be moved relative to the component being manufactured, for scanning a solidified region comprising a plurality of material layers, wherein one scanning depth corresponds to a multiple of the layer thickness, and an evaluating system, including a controller configured for determining a material characterization of an uppermost material layer of the solidified region, the controller is configured to:

recursively compare a preceding eddy-current scan of solidified region with a current eddy-current scan of the solidified region with a recursive algorithm to isolate the uppermost material layer from the multiple layer thickness of the current eddy-scan by comparing the current eddy-current scan as compared to a preceding eddy-current scan, wherein the preceding eddy-current scan of the solidified region is weighted exponentially according to depth, and wherein the controller is configured to detect defects comprising microcracks, micropores, segregations, foreign inclusions, and unmolten material are identified in the uppermost material layer of the solidified region.

8. The device according to claim 7, wherein the eddy-current array is positioned on a back side of a doctor blade.

9. The device according to claim 8, wherein the eddy-current array is an eddy-current linear array, which extends in the longitudinal direction of the doctor blade.

10. The device according to claim 7, wherein the eddy-current array has eddy-current sensors as individual sensors or half-transmission sensors in a hexagonal arrangement.

11. The device according to claim 7, wherein a shaking mechanism is provided with at least one piezoelement for placing the eddy-current array in shaking motion.

12. The device according to claim 7, further comprising an automatic distance control mechanism for adjusting the distance of the eddy-current array relative to the uppermost solidified material layer each time.

\* \* \* \* \*